United States Patent
Wei et al.

(10) Patent No.: US 9,993,532 B2
(45) Date of Patent: Jun. 12, 2018

(54) **BROAD SPECTRUM OF *STREPTOCOCCUS* LYASE AND USE THEREOF**

(71) Applicant: Wuhan Phagelux Bio-Tech Company Limited, Wuhan (CN)

(72) Inventors: Hongping Wei, Wuhan (CN); Hang Yang, Wuhan (CN); Jing Wang, Wuhan (CN); Junping Yu, Wuhan (CN)

(73) Assignee: Wuhan Phagelux Bio-Tech Company Limited, Wuhan (CN)

( * ) Notice: Subject to any disclaimer, the term of this patent is extended or adjusted under 35 U.S.C. 154(b) by 0 days. days.

(21) Appl. No.: 15/564,063

(22) PCT Filed: Apr. 12, 2016

(86) PCT No.: PCT/CN2016/079043
§ 371 (c)(1),
(2) Date: Dec. 18, 2017

(87) PCT Pub. No.: WO2016/165604
PCT Pub. Date: Oct. 20, 2016

(65) Prior Publication Data
US 2018/0104316 A1    Apr. 19, 2018

(30) Foreign Application Priority Data
Apr. 13, 2015 (CN) .......................... 2015 1 0171835

(51) Int. Cl.
| | | |
|---|---|---|
| *C12N 9/88* | (2006.01) | |
| *A23C 9/12* | (2006.01) | |
| *A61K 38/51* | (2006.01) | |
| *A61P 31/04* | (2006.01) | |
| *A61P 1/02* | (2006.01) | |
| *C12N 15/10* | (2006.01) | |
| *C12N 15/70* | (2006.01) | |

(52) U.S. Cl.
CPC .............. *A61K 38/51* (2013.01); *A61P 31/04* (2018.01); *C12N 9/88* (2013.01); *C12N 15/101* (2013.01); *C12N 15/70* (2013.01)

(58) Field of Classification Search
CPC .. C12N 9/88; A23C 9/12; A61K 38/51; A61P 31/04; A61P 1/02
See application file for complete search history.

(56) References Cited

FOREIGN PATENT DOCUMENTS

| | | |
|---|---|---|
| CN | 102181420 A | 9/2011 |
| CN | 103080307 A | 5/2013 |
| CN | 103122347 A | 5/2013 |
| CN | 103443269 A | 12/2013 |
| CN | 104726439 A | 6/2015 |

OTHER PUBLICATIONS

Patent Cooperation Treaty, International Searching Authority, Search Report and Written Opinion for PCT/CN2016/079043, 8 pages, Jul. 14, 2016.

*Primary Examiner* — Maryam Monshipouri
(74) *Attorney, Agent, or Firm* — Viksnins Harris Padys Malen LLP

(57) ABSTRACT

This invention discloses a lysin that can kill many species of Streptococci. A new lysin, ClyR, was constructed by the gene splicing method. The ClyR can effectively kill different species of Streptococci, including *Streptococcus pneumoniae, Streptococcus pyogenes, Streptococcus suis, Streptococcus uberis, Streptococcus agalactiae, Streptococcus dysgalactiae, Streptococcus mutans, Streptococcus equi*, and various Enterococci and *Staphylococcus aureus*. ClyR shows good stability and is not sensitive to EDTA and high concentration of NaCl. Moreover, the ClyR is active in a wide range of pH and maintains high activity in pH 5-11. Recombinant protein ClyR is well expressed in *E. coli* stain BL21 (DE3). High doses of ClyR showed no apparent toxicity in mice. Furthermore, administration of 0.8 mg per mouse once is able to completely protect the mouse infected with lethal doses of Group B Streptococci. The ClyR can be used alone or in combination with different forms of reagents and solutions, for the control of a variety of Streptococci and for the treatment of infections caused by these bacteria. It has a broad application prospect.

10 Claims, 4 Drawing Sheets

BROAD SPECTRUM OF *STREPTOCOCCUS* LYASE AND USE THEREOF

SEQUENCE LISTING

The instant application contains a Sequence Listing which has been submitted in ASCII format via EFS-Web and is hereby incorporated by reference in its entirety. Said ASCII copy, created on Dec. 11, 2017, is named 18555.001US1_SL.txt and is 4.062 bytes in size.

TECHNICAL FIELD

The invention belongs to the microbiology field, in particular relates to a kind of lysin that is capable of killing Streptococci, Enterococci and *Staphylococcus aureus*, and its coding gene, and the use thereof as antimicrobial.

BACKGROUND

*Streptococcus* is a class of spherical Gram-positive bacteria that cause many diseases in humans and animals. *Streptococcus pneumoniae* is the main pathogenic bacteria causing lobar pneumonia and other diseases. It more frequently causes bronchopneumonia among infants and children. *Streptococcus pyogenes* is widely distributed in nature, and is one of the most important human bacterial infection pathogens. It can cause a variety of suppurative inflammation, including scarlet fever, erysipelas, neonatal sepsis, meningitis, *Streptococcus* allergy and so on. Group B Streptococci, such as *Streptococcus agalactiae*, is one of the important pathogens of perinatal infection, which seriously threatens the health of the newborns. *Streptococcus. mutans* is the main pathogen of dental caries, which seriously threatens the oral health of human beings. At present, there is no effective vaccine for the prevention and treatment of dental caries. In addition, Streptococci can cause a number of important animal diseases and threaten animal husbandry seriously. *Streptococcus suis* disease is a zoonotic acute and febrile infectious disease, usually caused by group C, D, E, and L Streptococci. Mastitis, the most important disease of farming industry in dairy cows, is caused by four main pathogenic bacteria, *Streptococcus agalactiae*, *Streptococcus uberis*, *Streptococcus dysgalactiae* and *Staphylococcus aureus*. However, there is still lack of effective vaccine and treatment strategy today. From the above, we can see that *Streptococcus* species are varied and can cause a large number of diseases of human beings and animals.

Phage lysin is a type of cell wall hydrolase expressed in late stage after dsDNA phage infecting host bacteria. Usually the size of the lysin is 25 kD~40 kD. Structurally, lysin is composed of two independent functional domains, the N-terminal catalytic domain and the C-terminal cell binding domain (CBD) that determines cell binding sites. The two domains are linked by a small fragment. Sequence analysis shows that the catalytic domain of the same type of lysin is highly conserved, while the cell binding domain is variable, which provides the possibility to construct a new chimeric lysin. Lysins are highly specific and can only specifically identify and lyse specific species of bacteria. In addition, the cleavage site is very well conserved, and the specificity of the phage and bacterial coevolution makes it difficult for host bacteria to develop resistance to them. These lysins characteristics provide theoretical feasibility for the control and treatment of drug-resistant bacteria in clinical practice. Until now, a few natural lysins that acts upon Streptococci have been reported. These lysins can kill specific strains of Streptococci both in vivo and in vitro. However, these lysins usually have a narrow lytic spectrum, and most of them are difficult to be solubly expressed, or do not high active, and active in a narrow range of pH, generally in pH 5-8. At present, none of lysins reported is able to lyse *Streptococcus mutans* effectively. It is very importantly significant to look for lysins, which are soluble, able to be expressed in high level, and show broad spectrum of activity, for development of new anti-streptococcal drugs and to control of streptococcal infections in vitro and so on.

DISCLOSURE OF INVENTION one technical problem to be solved in this invention is to provide a lysin, which is capable of killing a high variety Streptococci. The lysin can kill Streptococci in vitro and in vivo, especially *Streptococcus pneumoniae*, *Streptococcus pyogenes*, *Streptococcus suis*, *Streptococcus uberis*, *Streptococcus agalactiae*, *Streptococcus dysgalactiae*, *Streptococcus mutans*, *Streptococcus equi* and various Enterococci and *Staphylococcus. aureus*. For the convenience of narration, we name this lysin as ClyR, and its coding gene as ClyR.

The nucleic acid sequence of the coding gene ClyR of *Streptococcus* lysin provided in the present invention is shown in SEQ.ID.NO.1.

The protein sequence of the *Streptococcus* lysin ClyR provided in the present invention is shown in SEQ.ID.NO.2.

The invention also provides a method for expression of soluble ClyR protein and its purification. The steps are as follows: the ClyR gene is cloned, and then ligated with expression vector pBAD24, then expression plasmid is transferred *E. coli* BL21 (DE3) and is expressed, the expressed protein is firstly purified by ion exchange, then treated with dialytic phosphate buffer (PBS).

The invention demonstrate that the ClyR has effect on killing a large variety of Streptococci and *Staphylococcus aureus* via vitro experiment, especially *Streptococcus pneumoniae*, *Streptococcus pyogenes*, *Streptococcus suis*, *Streptococcus uberis*, *Streptococcus agalactiae*, *Streptococcus dysgalactiae*, *Streptococcus mutans*, *Streptococcus equi* and various Enterococci and *Staphylococcus aureus*, which proves the high activity and broad spectrum anti-bacterial activity of this lysin. The invention also preliminarily tested the protective effect of ClyR in the experimental animal model mice infected with Group B *Streptococcus*, and tested the cytotoxicity, which initially confirmed the potential of the drug for the development of anti-streptococcal infections.

The invention has the following beneficial effects and advantages:

The ClyR according to the invention can be used for in vivo and in vitro killing of a large variety Streptococci and *Staphylococcus aureus*. ClyR can be expressed in *Escherichia coli* in soluble form, and has high enzyme activity and relatively high activity in the range of pH 5-11. It can kill Streptococci with broad spectrum, and has the potential to be applied to antimicrobial drugs in vivo.

DETAILED DESCRIPTION OF THE INVENTION

The present invention is further explained by the following examples, but the present invention is not to be limited by this.

We designed and synthesised a type of new *Streptococcus* lysin designated ClyR through the analysis of amino acid sequences of the catalyst domain and the cellar structure domain of *Staphylococcus* phage lysin.

The methods used in the following examples were standard experimental methods without special description. All primers used in experiments were provided by Invitrogen (Shanghai). DNA sequencing was performed by Invitrogen (Shanghai).

Example 1

Construction of the Lysin with Ability of Specifically Killing Streptococci

1) The ClyR gene sequence expressing lysin ClyR was totally synthesised by Genscript (Nanjing). The synthetic sequence was inserted into plasmid pUC57. The ClyR gene was used as a template. Restriction enzyme sites NcoI and XhoI were introduced at two terminals of the target gene. Primers were designed as below:

```
Forward primer:
                                        (SEQ.ID.NO. 3)
    5-TATACCATGGGCATGGCAGCAAATCTGG-3
          NcoI Reverse primer:
                                        (SEQ.ID.NO. 4)
    5-ATATCTCGAGTTTGAAGGTACCCCATGCGTTG-3
          XhoI
```

2 μl of gene was used as a template, 1 μg of each primer was added for PCR amplification, and the programme of PCR amplification was described as below:

(1) 94° C., 5 min;

(2) 94° C., 30 sec, 62° C., 45 sec, 72° C., 45 sec, 30 cycles;

(3) 72° C., 10 min.

Figure 1:
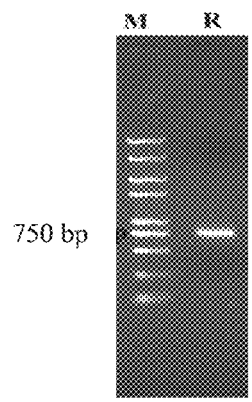
FIG. 1 shows the PCR amplification of the gene ClyR. M is the standard molecular weight marker. The arrow points to 750 bp. R is the band of the amplified ClyR.

PCR products were electrophoresed and recovered, the data of electrophoresis was shown in FIG. 1. The size of ClyR gene was 759 bp, which was same as the designed lysin.

2) The ClyR gene was ligated with expression plasmid pBAD24 to obtain a recombinant plasmid pB-ClyR, and then this recombinant plasmid was transferred into *E. coli* strain BL21(DE3).

3) Expression and purification of ClyR

Expression strain BL21(DE3)/pB-ClyR was induced by 0.2% L-arabinose to express the lysin under low temperature. Bacteria were collected, and then sonicated, the supernatant was obtained and precipitated by 33% ammonium sulphate. The precipitate was then dissolved in PBS and dialysed against PBS overnight. The dialysate had obvious anti-bacterial activity.

The crude extract after dialysis or the supernatant after sonication was passed through a HiTrap Q Sepharose FF column (GE Healthcare), and the effluent was collected. The effluent was then passed through a HiTrap SP Sepharose FF column, and the sample was eluted by using a gradient of 1M NaCl, and the elution peaks were collected separately. The fractions with activity were combined, and then dialysed against PBS overnight. The resulting sample was a purified enzyme.

Example 2

Verification of the killing effect of ClyR on standard *Streptococcus dysgalactiae* strain ATCC 35666

Figure 2:
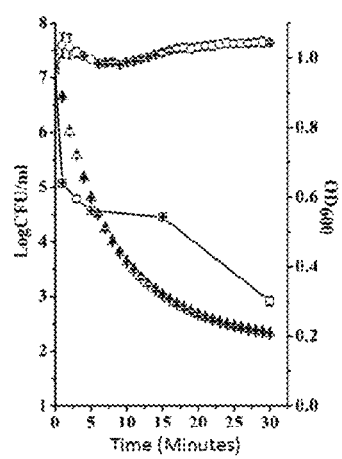
FIG. 2 demonstrates the kinetics of the killing effect of ClyR on *Streptococcus dysgalactiae* standard strain ATCC 35666 over time. The solid rectangle shows the change trend of Log CFU over time after *Streptococcus dysgalactiae* being mixed with ClyR. The hollow circle shows the change trend of $OD_{600}$ over time after *Streptococcus dysgalactiae* being mixed with buffer. The hollow triangle shows the change trend of $OD_{600}$ over time after *Streptococcus dysgalactiae* being mixed with ClyR.

An overnight culture of *Streptococcus dysgalactiae* strain ATCC 35666 was collected by centrifugation, and washed with PBS once, and then re-suspended in PBS. A certain amount of ClyR was mixed with the above bacteria culture, at the same time, the change of absorbance at 600 nm and the number of viable bacteria was monitored by a microplate reader. The mixture of buffer and *Streptococcus dysgalactiae* was used as a negative control. The final lysis curve was obtained as shown in FIG. 2. This result showed that ATCC 35666 strain was rapidly lysed by ClyR, as a result, absorbance at 600 nm was rapidly declined.

Example 3

Verification of the Effect of EDTA on the Activity of ClyR

An overnight culture of Streptococcus dysgalactiae strain ATCC 35666 was collected by centrifugation, and washed with PBS once, and then re-suspended in PBS. Bacteria suspensions were then divided into multiple parts, and different concentrations of EDTA were added, respectively, and then well mixed.

Figure 3:
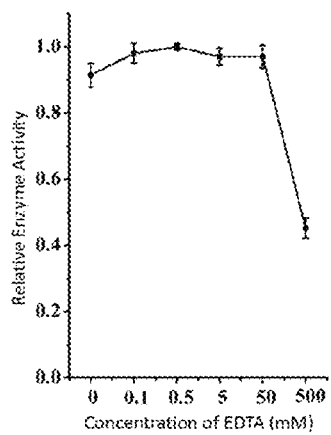
FIG. 3 is the result of the effect of EDTA on ClyR activity. *Streptococcus dysgalactiae* standard strain ATCC 35666 was re-suspended in PBS buffer with different EDTA concentration, and then mixed with the same concentration of ClyR to detect the change trend of $OD_{600}$ over time. The vertical coordinates indicate the relative activity of ClyR under different conditions.

A certain amount of ClyR was mixed with the above bacteria culture, at the same time, the change of absorbance at 600 nm of mixture was monitored by a microplate reader. The mixture of buffer and Streptococcus dysgalactiae was used as a negative control. After detection, the reduced values of $OD_{600}$ between each test group and the control group were calculated, the maximum reduced values of $OD_{600}$ was defined as 1, the reduced values of $OD_{600}$ in other groups were compared with said value, and then the relative enzyme activity was obtained. The final lysis curve was obtained as shown in FIG. 3. The results showed that EDTA had less effect on the activity of ClyR.

Example 4

Verification of the Effect of pH on the Activity of ClyR

Figure 4:
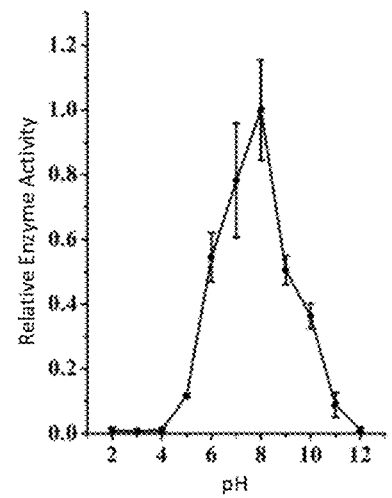
FIG. 4 is the result of the effect of pH on ClyR activity. *Streptococcus dysgalactiae* standard strain ATCC 35666 was re-suspended in the buffer with different pH, and then mixed with the same concentration of ClyR to detect the change trend of $OD_{600}$ over time. The vertical coordinates indicate the relative activity of ClyR under different conditions.

An overnight culture of Streptococcus dysgalactiae strain ATCC 35666 was collected by centrifugation, and washed once with PBS, and then re-suspended in buffer with different pH. A certain amount of ClyR was mixed with the above bacteria suspensions, at the same time, the change of absorbance at 600 nm of mixture was monitored by a microplate reader. The mixture of buffer and Streptococcus dysgalactiae was used as a negative control. After detection, the reduced values of $OD_{600}$ between each test group and the control group were calculated, the maximum reduced values of $OD_{600}$ was defined as 1, the reduced values of $OD_{600}$ in other groups were compared with said value, and then the relative enzyme activity was obtained. The final lysis curve was obtained as shown in FIG. 4. The results demonstrate that ClyR show good activity in pH range of 5-11.

Example 5

Verification of the Effect of NaCl on the Activity of ClyR

Figure 5:
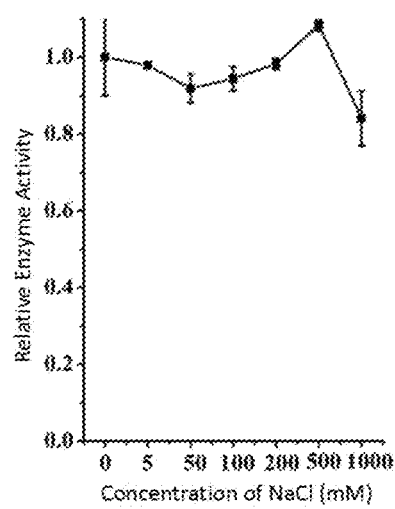
FIG. 5 shows the effect of NaCl on ClyR activity. *Streptococcus dysgalactiae* standard strain ATCC 35666 was re-suspended in the buffer with different NaCl concentration, and then mixed with the same concentration of ClyR to detect the change trend of $OD_{600}$ over time. The vertical coordinates indicate the relative activity of ClyR under different conditions.

An overnight culture of Streptococcus dysgalactiae strain ATCC 35666 was collected by centrifugation, and washed once with PBS, and then re-suspended in PBS. Bacteria suspensions were then divided into multiple portions, different concentrations of NaCl was added, respectively, and then well mixed. A certain amount of ClyR was mixed with the above bacteria suspensions, at the same time, the change of absorbance at 600 nm of mixture was monitored by a microplate reader. At same time The mixture of buffer and Streptococcus dysgalactiae was used as a negative control. After detection, the reduced values of $OD_{600}$ between each test group and the control group were calculated, the maximum reduced values of $OD_{600}$ was defined as 1, the reduced values of $OD_{600}$ in other groups were compared with said value, and then the relative enzyme activity was obtained. Final lysis curve was obtained as shown in FIG. 5. The results showed that NaCl had less effect on the activity of ClyR.

Example 6

Figure 6:
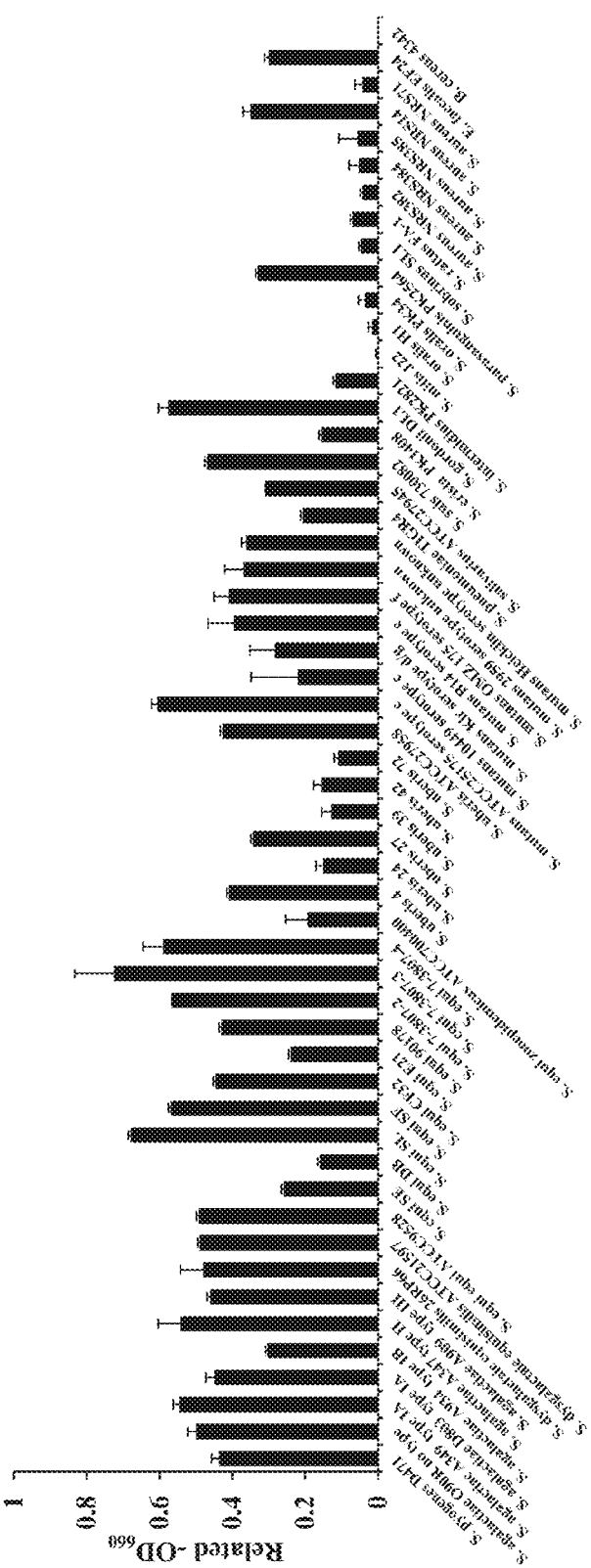
FIG. 6 demonstrates the result of the broad spectrum of ClyR killing Streptococci, *Staphylococcus* and other bacteria in vitro. The vertical coordinates indicate the decreased values of $OD_{600}$ after different strains being mixed with ClyR and incubated at 37° C. for 15 min.

Verification of Spectrum of Anti-Bacterial Activity of ClyR Against Streptococcus, Staphylococci and Other Bacteria Strains An overnight culture of different Streptococcus, Staphylococcus and other reference stains were collected by centrifugation, and washed with once PBS, and then re-suspended in PBS. A certain amount of ClyR was mixed with the above bacteria suspension, at the same time, the change of absorbance at 600 nm of mixture was monitored by a microplate reader for 15 minutes. The reduced values of $OD_{600}$ indicated the lytic effect against different strains. At the same time, the mixture of buffer and bacteria suspension was used as a negative control. The killing curve obtained from this experiment was shown in FIG. 6. The result show ClyR was able to rapidly kill multiple Streptococci (especially Streptococcus pneumoniae, Streptococcus pyogenes, Streptococcus suis, Streptococcus uberis, Streptococcus agalactiae, Streptococcus dysgalactiae, Streptococcus mutans or Streptococcus. equi), and also Staphylococcus, but there was no lytic activity against other tested strains.

Example 7

Figure 7:
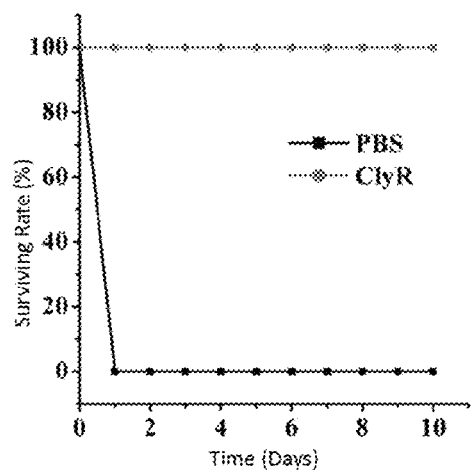
FIG. 7 shows the result of the killing effect of ClyR on Streptococci in vivo. 20 mice in each group were injected with lethal doses of *Streptococcus agalactiae*, individually. After 3 hours, the mice in the experimental group were injected with 0.8 mg ClyR intraperitoneally; while the mice in the control group were injected with an equal volume of PBS solution intraperitoneally after 3 hours. The survival rate of the mice in each group was observed each day.

Verification of the Anti-Streptococcus Activity of ClyR In Vivo approximately 20 to 22 g, 6 weeks old female BALB/c mice were used in this experiment; weights of mice were. Experimental mice (40 mice) were injected intraperitoneally with $6\times10^8$ of Streptococcus agalactiae strain. After 3 hours, mice were divided into two groups (20 mice in each group). The mice in the test group were injected intraperitoneally with 800 µg ClyR, and the mice in the control group were injected intraperitoneally with PBS buffer. The survival rate of the mice was observed every day, and the results were shown in FIG. 7. This result showed that ClyR was able to rapidly kill Streptococcus in vivo, therefore, the survival rate of the mice was increased.

Example 8

Verification of the No Cytotoxicity of ClyR

Figure 8:
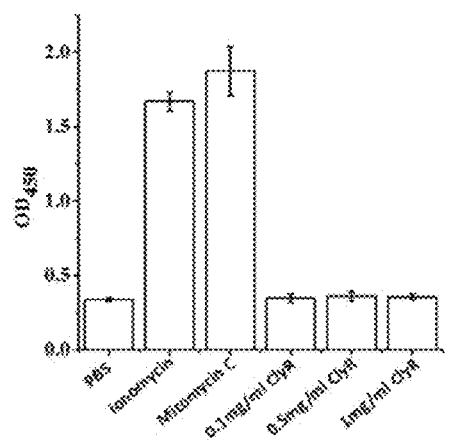
FIG. 8 shows results of the cytotoxicity results of ClyR. the concentrations of 0.1 mg/ml, 0.5 mg/ml and 1 mg/ml of ClyR are applied to Caco-2 cells respectively, no significant cytotoxicity is observed. Ionomycin and Mitomycin C which are well known to be toxic to these cells were used as positive controls.

Caco-2 cells were inoculated into 96 well plates at a concentration of $5\times10^3$ cells per well. After incubation for 24 hours, a certain concentration of ClyR (0.1-1 mg/ml), ionomycin (15 mg/ml) and mitomycin (15 mg/ml) were added into wells. After further incubation for 24 hours, the staining reagent WST-8 was added into wells. After standing, the absorbance at 450 nm were measured. The obtained results were shown in FIG. 8. The results showed that ClyR had no cytotoxicity in high concentration.

Example 9

Verification of the Elimination of Streptococcus in Milk Using ClyR

Figure 9:
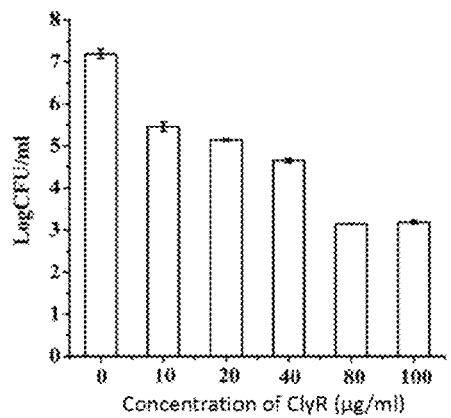
FIG. 9 demonstrate the result of the killing effect of ClyR on *Streptococcus* in milk. *Streptococcus dysgalactiae* ATCC 35666 was mixed with sterile milk and then treated with different concentrations of ClyR for 1 hour. Bacterial numbers on plates were counted after serial dilution.

An overnight culture of Streptococcus was collected by centrifugation, and washed with PBS once, and then re-suspended in sterile milk. Different concentrations of ClyR were mixed with the above bacterial suspensions, after mixed well, the reaction suspensions were incubated at 37° C. for 1 hour, and then the number of viable bacteria was calculated by serial dilution and counting on plates. Experimental results were shown in FIG. 9. The results showed that this enzyme was able to effectively eliminate Streptococcus in milk.

The invention claimed is:

1. An isolated and recombinant *Streptococcus* lyase ClyR, wherein the protein sequence of said lyase is shown in SEQ.ID.NO.2.

2. A vector comprising a ClyR gene coding *Streptococcus* lyase according to claim 1, wherein the DNA sequence of this gene is shown in SEQ.ID.NO.1.

3. A method of soluble expression and purification of *Streptococcus* lyase ClyR according to claim 1, characterized in that the ClyR gene is cloned and ligated with expression vector pBAD24, then expression plasmid transferred in *E. coli* BL21 (DE3) and is expressed; the expressed protein is firstly purified by ion exchange chromatography, and then treated with dialytic phosphate buffer.

4. A method to kill *Streptococcus, Enterococcus* and/or *Staphylococcus aureus*, comprising contacting the *Streptococcus, Enterococcus* and/or *Staphylococcus aureus* with lyase ClyR according to claim 1.

5. The method of claim 4, wherein the Streptococci is *Streptococcus pneumoniae, Streptococcus pyogenes, Streptococcus suis, Streptococcus uberis, Streptococcus agalactiae, Streptococcus, dysgalactiae, Streptococcus mutans* or *Streptococcus equi.*

6. The method of claim 4, wherein the *Streptococcus* is in milk.

7. A medicament comprising the *Streptococcus* lyase ClyR according to claim 1.

8. A method for the treatment of bovine mastitis comprising administering a medicament comprising the *Streptococcus* lyase ClyR according to claim 1.

9. A method for the treatment of dental caries comprising administering a medicament comprising the *Streptococcus* lyase ClyR according to claim 1.

10. An antibiotic, composition comprising the *Streptococcus* lyase ClyR according to claim 1.

* * * * *

SEQUENCE LISTING

<160> NUMBER OF SEQ ID NOS: 4

<210> SEQ ID NO 1
<211> LENGTH: 759
<212> TYPE: DNA
<213> ORGANISM: Artificial Sequence
<220> FEATURE:
<223> OTHER INFORMATION: Synthetic construct

<400> SEQUENCE: 1

```
atggcagcaa atctggcaaa cgcacaagca caagtgggca aatacatcgg cgacggtcaa    60
tgttacgcat gggttggttg gtggagcgcg cgtgtgtgcg gctatagcat ttcttacagt   120
accggtgatc cgatgctgcc gctgattggc gacggtatga acgcccattc gatccacctg   180
ggctgggatt ggagcattgc aaacaccggt atcgtcaatt atccggtcgg cacggtgggt   240
cgtaaagaag acctgcgcgt gggtgcaatc tggtgtgcaa ccgcttttag cggtgccccg   300
ttctataccg gccagtacgg tcatacgggc attatcgaat cctggtcaga taccacggtg   360
accgttctgg aacaaaacat tctgggctct ccggttatcc gtagtaccta tgacctgaat   420
acgtttctgt ccaccctgac gggcctgatt accttcaaac cgccgggtac ggtcgcacag   480
tctgcaccga atctggcagg ttcgcgtagc taccgtgaaa ccggtacgat gaccgtcacg   540
gtggatgcac tgaacgtgcg tcgcgctccg aatacctctg gcgaaattgt tgccgtctat   600
aaacgcggtg aaagttttga ttacgacacg gttattatcg atgtcaacgg ctatgtgtgg   660
gtttcctaca tcggcggttc aggcaaacgt aattatgttg caaccggtgc tacgaaagac   720
ggtaaacgct ttggcaacgc atggggtacc ttcaaataa                          759
```

<210> SEQ ID NO 2
<211> LENGTH: 252
<212> TYPE: PRT
<213> ORGANISM: Artificial Sequence
<220> FEATURE:
<223> OTHER INFORMATION: Synthetic construct

<400> SEQUENCE: 2

```
Met Ala Ala Asn Leu Ala Asn Ala Gln Ala Gln Val Gly Lys Tyr Ile
1               5                   10                  15

Gly Asp Gly Gln Cys Tyr Ala Trp Val Gly Trp Trp Ser Ala Arg Val
            20                  25                  30

Cys Gly Tyr Ser Ile Ser Tyr Ser Thr Gly Asp Pro Met Leu Pro Leu
        35                  40                  45

Ile Gly Asp Gly Met Asn Ala His Ser Ile His Leu Gly Trp Asp Trp
    50                  55                  60

Ser Ile Ala Asn Thr Gly Ile Val Asn Tyr Pro Val Gly Thr Val Gly
65                  70                  75                  80

Arg Lys Glu Asp Leu Arg Val Gly Ala Ile Trp Cys Ala Thr Ala Phe
                85                  90                  95

Ser Gly Ala Pro Phe Tyr Thr Gly Gln Tyr Gly His Thr Gly Ile Ile
            100                 105                 110

Glu Ser Trp Ser Asp Thr Thr Val Thr Val Leu Glu Gln Asn Ile Leu
        115                 120                 125

Gly Ser Pro Val Ile Arg Ser Thr Tyr Asp Leu Asn Thr Phe Leu Ser
    130                 135                 140

Thr Leu Thr Gly Leu Ile Thr Phe Lys Pro Pro Gly Thr Val Ala Gln
145                 150                 155                 160

Ser Ala Pro Asn Leu Ala Gly Ser Arg Ser Tyr Arg Glu Thr Gly Thr
```

-continued

```
                165                  170                  175
Met Thr Val Thr Val Asp Ala Leu Asn Val Arg Arg Ala Pro Asn Thr
            180                  185                  190

Ser Gly Glu Ile Val Ala Val Tyr Lys Arg Gly Glu Ser Phe Asp Tyr
        195                  200                  205

Asp Thr Val Ile Ile Asp Val Asn Gly Tyr Val Trp Val Ser Tyr Ile
    210                  215                  220

Gly Gly Ser Gly Lys Arg Asn Tyr Val Ala Thr Gly Ala Thr Lys Asp
225                  230                  235                  240

Gly Lys Arg Phe Gly Asn Ala Trp Gly Thr Phe Lys
                245                  250

<210> SEQ ID NO 3
<211> LENGTH: 28
<212> TYPE: DNA
<213> ORGANISM: Artificial Sequence
<220> FEATURE:
<223> OTHER INFORMATION: Synthetic construct

<400> SEQUENCE: 3
tataccatgg gcatggcagc aaatctgg                                    28

<210> SEQ ID NO 4
<211> LENGTH: 32
<212> TYPE: DNA
<213> ORGANISM: Artificial Sequence
<220> FEATURE:
<223> OTHER INFORMATION: Synthetic construct

<400> SEQUENCE: 4
atatctcgag tttgaaggta ccccatgcgt tg                               32
```